US 9,562,865 B2

(12) United States Patent
Schnablegger et al.

(10) Patent No.: US 9,562,865 B2
(45) Date of Patent: Feb. 7, 2017

(54) METHOD AND APPARATUS FOR ANALYSIS OF SAMPLES

(71) Applicant: ANTON PAAR GMBH, Graz-Strassgang (AT)

(72) Inventors: Heimo Schnablegger, Graz (AT); Josef Gautsch, Graz (AT); Wolfgang Gigerl, Eibiswald (AT)

(73) Assignee: Anton Paar GmbH, Graz-Strassgang (AT)

( * ) Notice: Subject to any disclaimer, the term of this patent is extended or adjusted under 35 U.S.C. 154(b) by 97 days.

(21) Appl. No.: 14/093,873

(22) Filed: Dec. 2, 2013

(65) Prior Publication Data

US 2014/0151569 A1    Jun. 5, 2014

(30) Foreign Application Priority Data

Nov. 30, 2012   (AT) .............................. A 50552/2012

(51) Int. Cl.
| G01N 23/05 | (2006.01) |
| G01N 23/20 | (2006.01) |
| G01N 23/201 | (2006.01) |
| G01N 23/202 | (2006.01) |

(52) U.S. Cl.
CPC ............ G01N 23/20 (2013.01); G01N 23/201 (2013.01); G01N 23/202 (2013.01)

(58) Field of Classification Search
CPC ... G01N 23/201; G01V 5/0025; G01V 5/0016
USPC ..................................... 378/86–90
See application file for complete search history.

(56) References Cited

U.S. PATENT DOCUMENTS

| 6,163,592 A * | 12/2000 | He .......................... G01N 23/20 378/70 |
| 6,881,537 B1 | 4/2005 | Goudsmit |
| 7,295,650 B2 * | 11/2007 | Lange .................. G01N 23/201 250/390.01 |
| 2011/0122995 A1 * | 5/2011 | Ferro, Jr. ............. A61B 6/4429 378/62 |
| 2014/0067316 A1 * | 3/2014 | Ishibashi ................ G06F 17/00 702/150 |

FOREIGN PATENT DOCUMENTS

| DE | 1002138 T1 | 6/2001 |
| DE | 10317677 A1 | 11/2004 |

* cited by examiner

*Primary Examiner* — David J Makiya
*Assistant Examiner* — Kenneth J Malkowski
(74) *Attorney, Agent, or Firm* — Laurence A. Greenberg; Werner H. Stemer; Ralph E. Locher

(57) ABSTRACT

A method and a device examine a sample with radiation emitted from a radiation source, which is directed to the sample carried by a sample holder via a beamforming unit and detected by a detector and evaluated in an evaluating unit. Prior to the examination of the sample, at least one of the following components, including the radiation source, beamforming unit, sample holder, detector, and a primary beam stop, are spatially oriented and/or positioned in relation to at least one of the other components and/or in relation to a predefined fixed point and/or in relation to the optical path with a control unit via actuating drives. The radiation intensity measured by the detector, in a predefined detector range, and/or a value derived therefrom is used for establishing a control variable conferred from the control unit to the actuating drives assigned to the components.

16 Claims, 3 Drawing Sheets

METHOD AND APPARATUS FOR ANALYSIS OF SAMPLES

CROSS-REFERENCE TO RELATED APPLICATION

This application claims the priority, under 35 U.S.C.§119(e), of Austrian provisional application No. AT50552/2012, filed Nov. 30, 2012; the prior application is herewith incorporated by reference in its entirety.

BACKGROUND OF THE INVENTION

Field of the Invention

The invention relates to a method and a device for examining a sample with radiation emitted from a neutron or X-ray radiation source, directed to the sample carried by a sample holder via at least one beam-forming unit, preferably beam-forming optics and/or beam-limiting optics, detected by a detector and evaluated in an evaluating unit.

The elastic scattering of X-ray radiation is used for non-destructive characterization of the structure of various sample materials. This kind of scattering-angle measurement can be conducted by X-ray radiation as well as, in a comparable manner, by neutron radiation. The invention can be implemented using both kinds of radiation.

X-ray scattering occurs when a beam of X-ray radiation impinges on an inhomogeneous, powdery, liquid, and/or solid material having a structure which is larger than the wavelength of the X-ray radiation employed. The X-rays penetrate into the sample, and the material being studied interacts with the X-ray beam, resulting in scattering. This results in characteristic interference images; the sum of waves scattered under a certain angle is characteristic of the size and symmetry of the scattering particles.

In principle, two different scattering geometries can be employed for small-angle scattering. Either the samples are positioned at a small angle with respect to the measurement beam, the measurement being performed at a grazing incidence close to the critical angle of total reflection and the pattern of the scattered radiation being recorded, or the sample is positioned so as to have the beam transmitted through it. With the first method, information is obtained about the surface structure of the sample, while with transmission scattering the nanostructure of the overall sample volume is analyzed.

Measurement devices of known and inventive kinds typically contain a neutron or X-ray source with adequate optics. As beam-generating sources, for example, stationary X-ray tubes, rotating anodes or a synchrotron can be used. For focusing or forming the beam and for monochromatization, for example, one-dimensional optics, such as Goebel mirror, or two-dimensional arrangements, such as those according to Kirkpatrick-Baez, are used. Convergent, focused, slightly diverging and parallelized bundles of rays can all be used for measurement. The focus of the measurement radiation can be in the plane of the sample to be examined or in the detector plane.

The measurement beam can be additionally shaped and/or masked out using an arrangement of apertures/diaphragms and/or a collimation system in order to send a parallel bundle of measurement beams as free of interfering scattering portions as possible for examination onto the sample to be examined. After interacting with the sample, the scattering image is measured using an X-ray detector, and the measured intensities are delivered to an evaluating unit. As only a small part of the measurement beam impinging on the sample is scattered, the unscattered portion of the measurement radiation, i.e. the primary beam, is masked out from the detector using a primary beam stop in order not to damage the detector.

Actual aberrations from an ideal scattering experiment are corrected using different mathematical corrections each applicable for the beam shape and scattering geometry selected.

One-dimensional detectors such as photo diode arrays, which detect the intensity distribution in a line perpendicular to the primary beam can be used as well as 2-dimensional arrangements such as CCD cameras, image plates or X-ray films.

FIG. 1 shows the basic design of small-angle scattering measurements based on a known classic Kratky camera, as described, for example, in German patent DE 1002138 B1 (corresponding to U.S. Pat. No. 6,881,537). The radiation emitted from a radiation source 0 is focused in subsequent optics 1 onto a sample 3 or a detector 5, which is positioned at a distance S from the sample 3 carried by a sample holder 7 and has an evaluating unit 30 connected thereto. There is a primary beam stop 4 in front of the detector 5. Slightly diverging beams can also be used, as the angle of aperture is small and sufficient intensities are available after beam limitation. Due to constantly present roughness's of the optics used and to construction tolerances, the bundle of beams thus obtained is usually additionally limited after the optics and optionally collimated in a collimator 2. Diaphragms used for finely masking out X-rays always emit scattering radiation themselves, which becomes very intense especially under small angles. For this reason, a number or combination of diaphragms successive in the optical path are usually used. For example, a slit collimator can be used as a combination of diaphragms, which contains two blocks for masking out and collimating the measurement beam.

When examining samples, the intensity of measurement radiation directed to the sample should be as high as possible. In order to achieve this, however, the resolution towards small angles required for each individual measurement problem needs to be taken into account. Apart from production tolerances of individual components like collimation block, diaphragms, beam optics, etc., the focused X-rays emitted by the source will also change due to characteristics of the sources and the components that are subject to change by time, such as temperature influences and aging phenomena. In addition, in a modular system, the change of individual components, such as source, beam optics, sample holders, etc., requires adjustments, which need to be able to be made as quickly and as comfortably for the operator as possible.

Mechanisms for adjusting the components are known in prior art. For example, German patent DE 103 17 677 (corresponding to U.S. Pat. No. 7,295,650) illustrates adjustment of the primary beam stop in z-direction using mechanical devices. Adjustments can be made using manually operated mechanical precision regulators or micrometer screws as well as via spindle drives and electrical stepper motors.

In order to protect the sensitive detector, the radiation intensity emitted from the source can be reduced upon adjustment of the system. If reduction of the intensity emitted from the source that is used is either not desired or not possible, reduction can be done by an absorber inserted between the source and the beam-focusing optics. If sensitive detectors are used, the memory map of which is available only by separate reading, such as image plates, or if the radiation of the sources is not supposed to be modified in its intensity, a support detector can be used alternatively in the place or in front of the detector, for which photo diodes, X-ray films or X-ray fluorescent screens find use, for example.

At present, a user will, prior to measurement or in between consecutive measurements, adjust the individual components of a device manually in a predefined sequence for adequate intensity on detector plane and, to do so, read the intensities measured at the detector in the course of change and/or at every adjustment step. These adjustment steps are described to the user in the manual including the required position of the image and/or intensities of primary beams and/or scattering images at the detector. This adjustment procedure thus requires a highly trained and experienced user, who makes all necessary adjustments manually with sure instincts and coordinates the individual components such that an optimal adjustment result is achieved with respect to the following measurement. This procedure is lengthy and error-prone, the individual components may even be destroyed due to faulty adjustment, and X-rays can exit from the device into the environment in the case of faulty adjustments.

SUMMARY OF THE INVENTION

It is accordingly an object of the invention to provide a method and an apparatus for analysis of samples that overcome the above-mentioned disadvantages of the prior art devices and methods of this general type.

These problems are solved according to the invention in a method of the above kind by orienting and/or adjusting with respect to its/their position in space at least one, preferably several, in particular all, of the following components in relation to at least one of the other components and/or in relation to a predefined fixed point and/or in relation to the optical path with a control unit via actuating drives prior to examining the sample: radiation source and/or beam-forming unit and/or sample holder and/or detector and/or optionally a primary beam stop upstream of the detector. The radiation intensity measured by the detector, in particular in at least one predefined detector range, and/or a value derived therefrom is used for creating a control variable sent from the control unit to the control circuits of the actuating drives assigned to each individual component.

Using the inventive procedure it is possible to perform adjustment of the device quickly and accurately, optionally following a dictated protocol, and to initialize and/or prepare a subsequent examination with high accuracy. According to the invention, adjustment of the inventive device becomes easy to handle for the user, particularly if the entire adjustment process is carried out in an automated manner via control circuits and controllable components. To achieve that, the intensity occurring at the detector and/or determined using the intended evaluating unit and/or values associated therewith and/or derived therefrom are used as control variable for the individual components of the device.

To achieve that, a plurality, or preferably all, of the adjustable components are each equipped with at least one controllable actuating drive. The actuating drives communicate with the control unit connected to the detector and/or the evaluating unit and are preferably controlled via the control variables "intensity at the detector" and/or "position of the image at the detector".

According to the invention, the individual components can each by adjusted automatically according to an adjustment program included in the control and/or evaluating units, with the entire adjustment procedure being advantageously carried out step by step automatically for each individual component.

Even when only one of the components of the inventive device is adjusted using the intended control unit, facilitation and specification of the adjustment process will occur. The radiation intensity used as a control variable reacts very sensitively to non-exact adjustment, hence it is possible to quickly obtain an optimum value for proper and/or required adjustment of the respective component. Adjustment of one or more components can be carried out in a predefined sequence of adjustment steps or in accord with the problem in question.

It is of advantage that no adjustment steps and/or settings that are dependent on the user are required. Thanks to automatic adjustment, absolute positions or adjustment intensities can be reconstituted in a reproducible manner; this guarantees comparability of measurements in the case of serial examinations, for example, of nanoparticles.

It is of advantage if the individual components are adjusted, optionally independently, to a predefined starting position before conducting a measurement, or if they are in a defined starting position, while those values of this starting adjustment that correspond to the position and/or orientation of each component are used as starting values for adjustment.

The initial settings of the adjustment process are thus clearly defined, serving as the basis for the following special adjustment.

It is useful to compare the radiation intensity determined at the detector and/or values derived therefrom with saved set values and to adjust the individual components with the actuating drives based on this comparison and/or to approximate the radiation intensity measured in the at least one predefined detector range to a predefined value, in particular a maximum value, during adjustment of the individual components and/or to determine and/or use the signal/noise ratio and/or the absolute intensity in the integral, two-dimensional image at the detector and/or the intensity of single intensity maximums in the scattering image and/or, especially when using a one-dimensional detector that is moved over the measured angular range, local intensity maximums as the values derived from the measured radiation intensity.

The measured intensities or any values derived therefrom can directly be used for determining the control variables for the actuating drives, as long as these values have significant dependency on the respective position and/or orientation of the respective component.

In order to obtain maximum variety of readjustment options for adjustment and to take all types of adjustable components into account, it can be intended to readjust the components in the direction of the optical path and/or in a plane perpendicular thereto and/or for adjustment in terms of their position in space and/or to readjust them in their orientation in terms of the axis of the optical path and/or to twist them, in particular around the axis of the optical path, and/or to tilt them with respect to that axis.

In order to increase the precision of adjustment, it can be intended to measure the X-rays impinging on the detector for determining the control variables in a variety of detector ranges, while optionally the course of radiation intensity is integrated over predefined detector ranges.

According to the invention, a device of the kind mentioned above is characterized in that at least one component, preferably a number of components or each of the components, including radiation source and/or beam-forming unit and/or beam-limiting unit and/or sample holder and/or detector and/or optionally a primary beam stop upstream of the detector, is connected and readjustable with at least one, in particular to at least one individual, actuating drive, which can be supplied with actuating signals from a control unit. The control unit has an input for measured values of radiation intensities determined in at least one predefined detector range of the detector and/or values derived therefrom and produces the actuating signals based on these measured values.

The design of the device allows for quick, accurate and safe adjustment of the components. By dictated protocols, faulty adjustments can be excluded from the beginning. For safety reasons, predefined limits can be set to the adjustment moves of the actuating drives. It is possible to adjust the individual components independently and accurately step by step and/or in a predefined sequence.

Simple and quick adjustment of the device is accomplished when the control unit has an input for the respective adjustment values corresponding to the orientation and/or position of the components. These actual values either are present saved in memories or can be determined by measurement units connected to the control unit, or are provided and/or obtainable by the actuating drives and/or the control unit has a comparator, by which the measured values of the radiation intensity determined in the predefined detector ranges are comparable to actual adjustment values saved and/or determined for the individual components.

In connection with the components to be adjusted, it is of advantage if they are provided in a form adjustable to all spatial directions, and it is particularly useful for the beam-forming optics and/or the beam-limiting optics and the radiation source to be shiftable with respect to one another in the three spatial dimensions and/or rotatable around the optical axis and the optical path, respectively, and/or tiltably supported and readjustable in a driven manner.

Depending on type and design of the individual components, orientation and position play an important role, and it can be intended that, for adjusting the beam-forming and/or beam-shaping optics, these optics are provided in the form of diaphragms insertable and/or tiltable into the optical path or adjustable with respect to their gap width, and/or that the sample holder and/or the sample and/or the primary beam stops are carried by a carrier unit insertable into the optical path in a plane perpendicular to the optical path and/or tiltable into the optical path and/or that the mutual distance between the radiation source and the sample holder and/or the detector and/or the distance between the sample holder and the detector is adjustable using the actuating drives assigned to the respective components depending on the measured value of the radiation intensity and/or a value derived therefrom.

Other features which are considered as characteristic for the invention are set forth in the appended claims.

Although the invention is illustrated and described herein as embodied in a method and an apparatus for analysis of samples, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
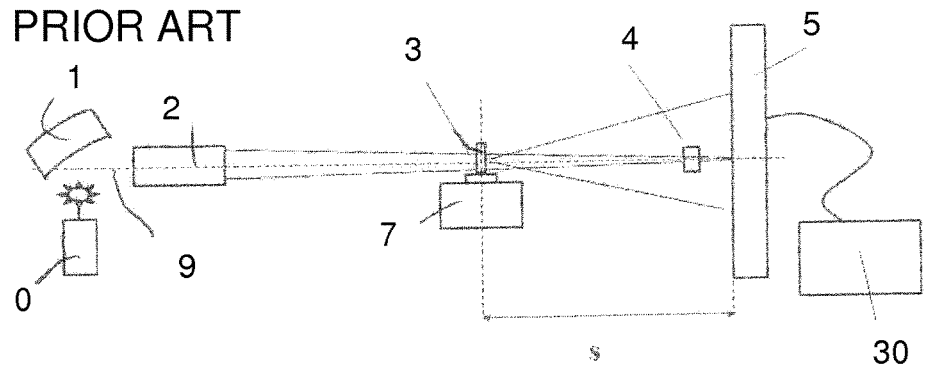
FIG. 1 is an illustration showing a basic design of small-angle scattering measurements based on a classic Kratky camera according to the prior art.
Figure 2:
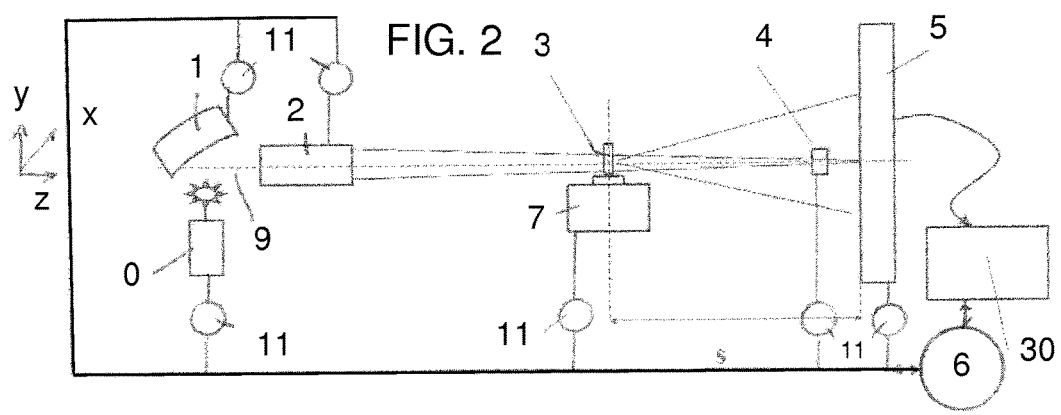
FIG. 2 is a schematic showing a design of a device according to the invention.

Referring now to the figures of the drawings in detail and first, particularly to FIG. 2 thereof, there is shown a basic design and the essential components of an inventive X-ray examination device which can be used to conduct the inventive method. The device is based on the device according to FIG. 1, supplemented by a control unit 6, by which actuating drives 11 for individual components 0, 01, 1, 2, 4, 5, 7 can be controlled. Several actuating drives 11 can be attributed to each component, for example, to adjust the component to various directions in space. In a simple embodiment, the actuating drive 11 can adjust an arrangement movable along an x-y plane having a holder for the component to be adjusted.

When examining samples 3, most of the time a maximum intensity of measurement radiation is supposed to be directed to the sample 3, while the resolution for each individual measurement problem towards small angles has to be taken into consideration. Thus, the requirements placed in the adjustment are high. It is also important to determine the current position of the components. The current position of each component can be determined or obtained at any point in time by adequate position detection device, such as position sensors or the position of the actuating drives 11 per se, in particular if the actuating drives 11 report the position and/or orientation of the component back to the control unit 6 and/or the evaluating unit 30. However, the determination of position can also be accomplished based on a resting position without absolute determination of the position, as it is the mutually relative position of the components that is relevant in this case.

Control of the actuating drives 11 is advantageously carried out by evaluating the intensity and/or intensity distribution recorded at the detector 5, comparing the obtained intensity measurement value with a set value for optimum adjustment position, preferably within the evaluating unit 30, and then moving the respective component. Appropriate control algorithms are predefined. The respective component is moved by the actuating drive 11, until the intensity and/or intensity distribution measured at the detector 5 corresponds to the set value or approximates it as closely as possible.

As the detector 5, a CCD array or a photodiode array or other position-sensitive detectors are preferably used, which support adjustment by recording images resolved according to their location, optionally in connection with image recognition software. A point-shaped detector that is being moved along the primary beam can also be used as the detector.

The method of adjusting the components in a small- and/or wide-angle measurement device advantageously begins after incorporating the desired components in a modular system or, in a stationary system without changing possibilities, by adjusting the radiation source 0 and the beam-forming optics 1. Depending on the optics used, either the radiation source 0 and/or the beam-focusing optics 1, such as mirrors, Goebel mirror, 2D optics, 3D optics, or the like, are oriented relative to one another, such that a primary beam with maximum intensity is created, which is then directed through the other components of this device. According to the invention, the first step can be automated by rotating and/or tilting the optics 1 or adjusting the radiation source 0 in the plane vertical to the z-axis of the device with the actuating drives 11, at least when replacing the radiation source 0 and/or the focusing optics 1. The z-axis is typically equal to the course of the optical path 9. This step can be controlled using the control unit 6. For adjusting the radiation source 0 and the beam-forming optics 1, usually the collimating and/or beam-limiting optics 2 is removed. This is either done manually or by extending the beam-limiting optics 2 containing a collimator and diaphragms, the sample holder 7, the primary beam stop 4 or, according to the invention, automatically by moving these components using the actuating drive 11 to a position which does not limit the measurement beam. To this end, usually an absorber 01 is used, which can also be brought into position by an actuating drive 11.

When adjusting the beam-limiting optics 2, such as slit collimators in the form of blocks or individual beam-limiting components, the primary beam stop 4 is moved from its measurement position using an actuating drive, and adjustment of the collimating element is done by tilting the same relative to the z-axis of the camera using the actuating drive 11.

The diaphragm elements or collimation elements of the optics 2 can be arranged like the other components by mounting within a housing or on a holder and moved using actuating drives 11, e.g. in the form of servomotors, linear motors and/or magnetic drives.

Figure 3:
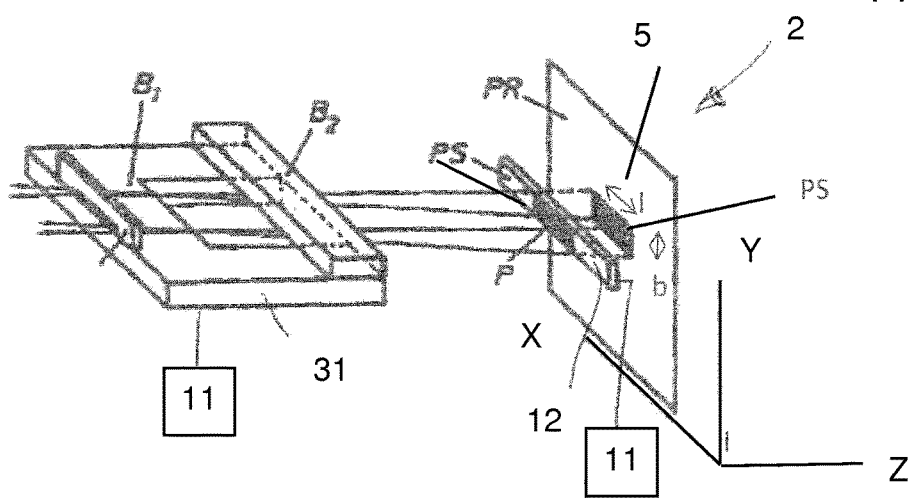
FIG. 3 and FIG. 3A are perspective views showing adjustable collimator and diaphragm units, using which can accomplish limitation and/or collimation of radiation.

FIG. 3 shows the arrangement of two collimation blocks B1 and B2 arranged on a carrier 31 and limiting the beam and a primary beam stop 12. The members collimation blocks B1 and B2 and primary beam stop 12 can be taken together in a housing or frame to form a unit and/or to form the beam-limiting optics 2 and carried by the carrier 31. This unit can be tilted relative to the optical axis during adjustment using the actuating drive 11. This can either be done by tilting the entire optics 2 or by tilting a frame carrying the other components, radiation source 0, the optics 1, the beam stop 4 and the detector 5, in which these components are arranged in a fixed manner along the optical axis 9, i.e. in parallel to the z-direction, as what matters is merely the relative position and orientation of the individual components with respect to one another. Adjusting, as changing the diaphragm position, is done automatically using the actuating drives 11 operated by the control unit 6.

Figure 3A:
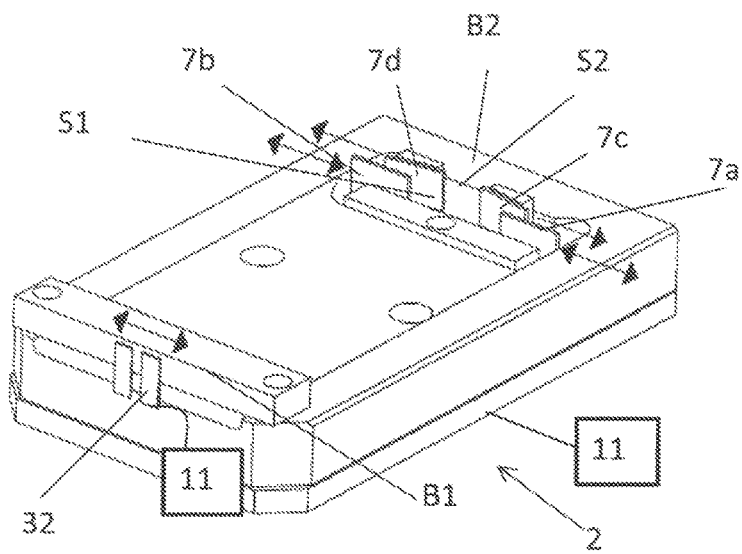
Figure 3B:
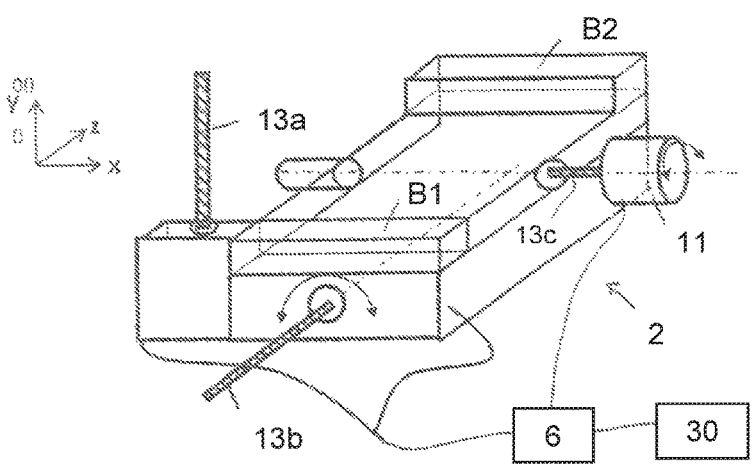
FIG. 3B is a perspective view of adjustable optics.

FIG. 3A shows beam-limiting optics 2, containing two tiltable collimation blocks B1 and B2 as well as one adjustable inlet diaphragm 32 and adjustable outlet diaphragms 7a, 7b, 7c and 7d. Tilting and adjusting the diaphragms can be accomplished using the actuating drives 11, which are indicated here like in the other figures. FIG. 3B shows optics 2, which are adjustable using servomotors 11 via spindle drives 13a, 13b and 13c in all spatial directions and tiltable around all spindle axes.

In order to achieve facilitated adjustment, optics 2 can be shifted along the y-axis using an actuating drive 11 to adapt the level of the diaphragm to the actual primary beam, while separately; a rotation around the z-axis can be accomplished using an actuating drive 11 to adjust the position of the collimated beam in the x-y plane. Adjustment of the adjustable elements of a collimation element can be accomplished by shifting the diaphragms using an actuating drive 11 along the x-axis as well as by adjusting the diaphragm gap.

Figure 4:
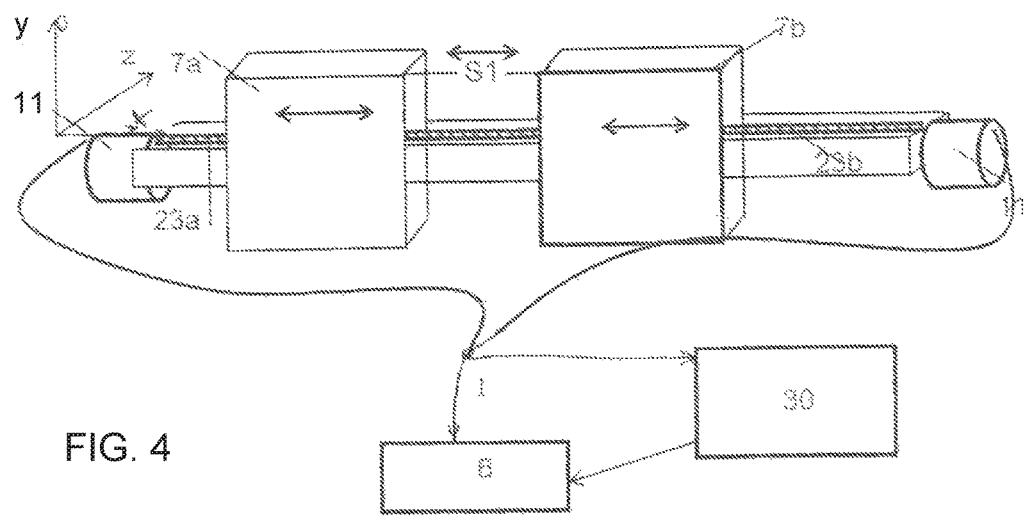
FIG. 4 is an illustration showing optics with slidable diaphragms.

As shown in FIG. 4, the diaphragms 7a and 7b of optics 2 can be movably mounted on a rail and/or holder in parallel to the x-direction. The actuating drives 11 can be used to change the distance between the diaphragms 7a and 7b and thus also the gap width S1. The actuating drives 11 drive the spindles 23a and 23b, on which the two diaphragms 7a and 7b are mounted. In addition, the position of the gap can be shifted along the x-axis. This is done for adjusting the gap relative to the optical path 9 of the primary beam through the slit collimation blocks B1 and B2. The collimation blocks B1, B2, and/or the entire beam-limiting optics can be adjusted by rotation around the z-axis and by rotation around the x-axis, each with specifically disposed servomotors 11.

If, for example, adjustment is done using actuating drives 11 having stepper motors and spindle drives, the stepper motors can be driven by the evaluating unit 30 and/or the control unit 6 via control pulses, until the desired position is achieved for the diaphragms 7a, 7b with respect to the slit collimation blocks B1 and B2.

For example, the gap width S1 can be calculated from the open or closed end position of the diaphragms 7a, 7b by counting the motor steps and known feed of the spindles 23a, 23b in the control unit 6 and/or the evaluating unit 30. Alternatively, the distance between the two diaphragms 7a, 7b can be determined using an appropriate length measurement system, such as an optical path sensor or a distance measuring device.

The position of the sample 3, which is arranged on or accepted by any sample holder 7, can be adjusted, for which first the sample holder 7 is placed in the position assigned for it. Various sample holders, such as changing cells, cuvettes, capillary holders, etc., can be provided. Sample holders 7 for measurements in a grazing incidence can also be used. Rotary movements, tiltings and grid movements can be conferred to the sample holder 7, and thus the sample 3, by actuating drives 11 relative to the optical path 9 in order to allow spatially resolved examinations.

A changing system can be provided for directing, fixing and incorporating the sample holder 7, and it can have guiding pins, screwed joints and the like, which place the sample 3 in a predefined starting position with respect to the sample holder 7.

Optionally the sample holder 7 can be equipped with a contactless sensor or chip, which optionally provides calibration data of the sample holder and can be recognized automatically. This data can be used as position and orientation measurement values in order to place each respective sample holder 7 that is movable in all directions in space and also arranged in a rotatable manner in the appropriate position using the actuating drives 11.

Figure 5:
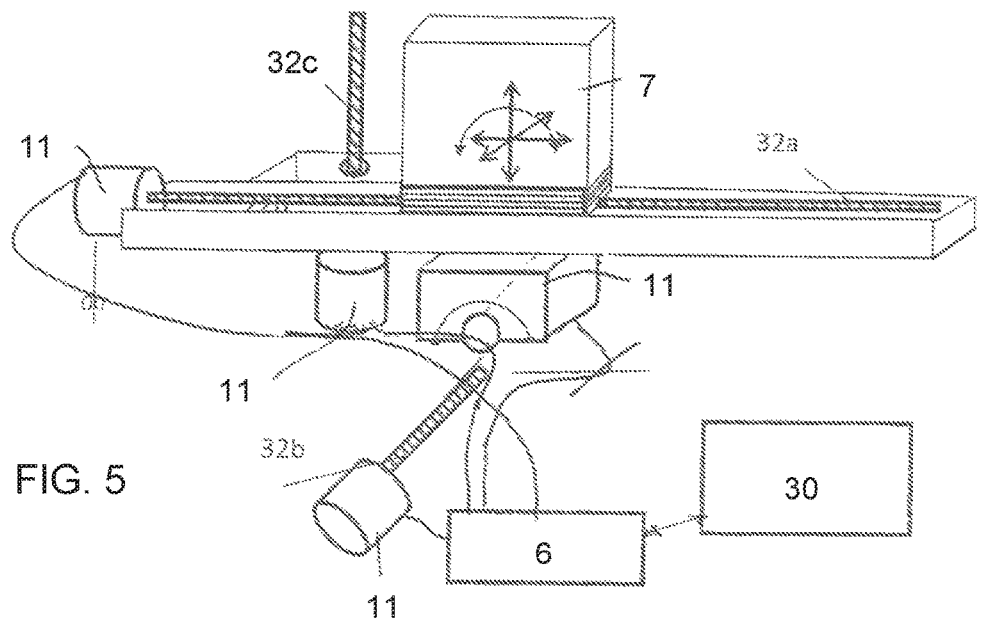
FIGS. 5 and 6 are illustrations showing a sample holder adjustable with actuating drives.

FIG. 5 shows such an arrangement with actuating drives 11, which operate the respective spindles 32a, 32b and 32c for translation of sample 3 in y-direction, translation in z-direction and translation in x-direction. At the same time tilting the sample holder 7 around the z-axis is possible using an actuating drive 11. Controlling the movements of the actuating drives 11 can be done by a predefined number of steps with a pulse generator.

If a movable detector 5 is used in the system, the desired scattering angle range to be measured can optionally be accomplished by selecting the distance S between the sample 3 and the detector 5. Setting the distance between the sample 3 and the detector 5 can be done by shifting the sample 3 and/or the sample holder 7 on a sample bench and/or shifting the detector 5 to the appropriate position automatically using the actuating drives 11 according to instructions. This way a fully automatic measurement with different angle ranges can be achieved by changing the distance between the sample 3 and the detector 5 and then evaluating the recorded spectra supported by automation and standardizing the measurements with respect to one another.

Figure 6:
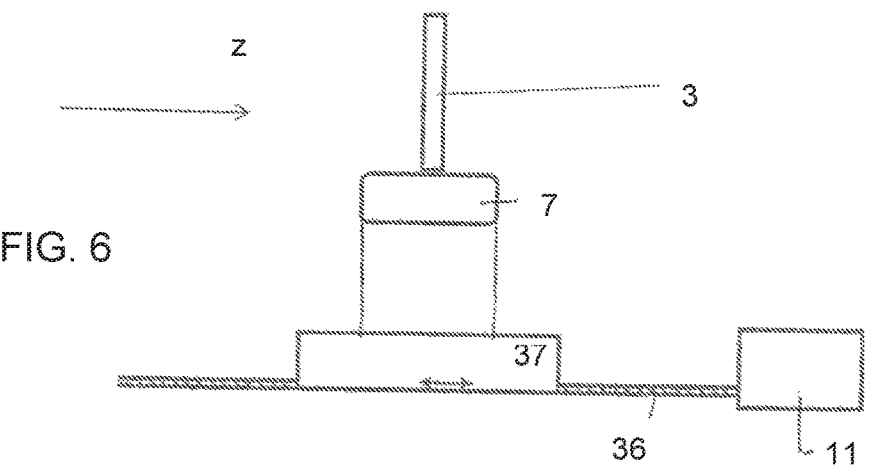

FIG. 6 shows an adjustable sample holder 7 on a bench 37 movable in z-direction, in which the actuating drive 11 drives, a spindle 36 and thereby moves the sample bench 37 along the z-axis. Thus, the distance between the sample 3 and the detector 5 can be changed and the sample 3 shifted along the optical axis 9. The sample bench 37 can be an integral part of the sample holder 7 or part of a removable sample changer. An entirely modular configuration is also possible.

The primary beam stop 4 has to be able to mask out a slit-shaped primary beam when the diaphragm gap is open. Primary beam stops 4 for a slit-collimated beam of varying line length and a point-collimated beam can be arranged interchangeably in a holder.

Figure 7:
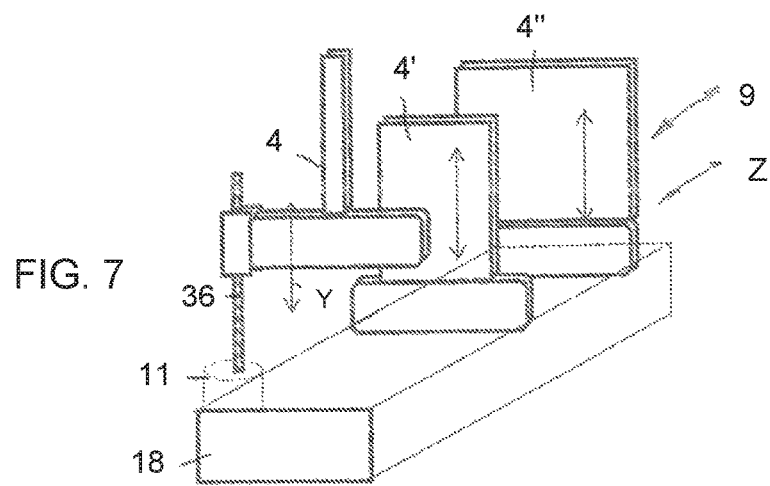
FIG. 7 is a perspective view of an adjustable primary beam stop.

In order to fully automate the device, an automated change of different primary beam stops 4, 4', 4" using a changing device 15 operated by the actuating drives 11 can be provided, i.e. the respective primary beam stop 4 is movable to and from the optical path 9 using an actuating drive 11 with a spindle drive 36. Reference numeral 18 designates a rack of the device, which is able to support the components and actuating drives. Alternatively, a multipartite embodiment of the primary beam stop 4 can be implemented. In this case, at least one primary beam stop 4 is available for adjustment in a plane vertical to the optical path 9. The beam stop 4 of choice is placed in its position in the measurement plane using the actuating drive 11 optionally from below and registered in y-direction with the measured intensity at the detector 5 by the primary beam. Optionally the orientation of the beam stop 4 has to be adapted with respect to the position of the gap at the detector 5 in the x-y plane by rotating around the z-axis using an actuating drive 11. Preferably, the beam stop 4 is introduced to the optical path 9 from below in the x-y plane. Each primary beam stop 4 has a separate feed in y-direction as shown in FIG. 7 for the primary beam stop 4, which is adjustable using an actuating drive 11 with the spindle 36.

The entire adjustment procedure can be automatic, for example, by selecting the control variable gradually or by defining absolute values. Control is done advantageously, for example, via "smallest detectable scattering angle" or "desired intensity at the detector" or a "desired" resolution.

A program present in the control unit 6 and/or in the evaluating unit 30 can also provide the user with fully defined measurement programs, e.g. for standard characterization of samples. The automated run of several different adjustment routines including measurement and subsequent joint evaluation of structural data, for example, of nanoparticles can span several orders of magnitude, as exemplified in detail as follows:

| Selection of automatic measurement program | "Characterization of isotropic nanoparticles with an anisotropic internal crystalline structure" |
| --- | --- |
| Adjustment routine 1 | Automatic moving of sample holder, adjustment of slit collimator and 2D optics to maximum gap length and minimum height, automatic adjustment of primary beam stop |
| Measurement 1 | Acceptance of isotropic small-angle scattering with minimum $q_{min}$ |
| Adjustment routine 2 | Adjustment of slit collimator and 2D optics to minimum gap length (resolution of anisotropic structure and greater height), adjustment of primary beam stop |
| Measurement 2 | Acceptance of isotropic/anisotropic small-angle scattering |
| Adjustment routine 3 | Adjustment of slit collimator and 2D optics, moving sample to larger distance |
| Measurement 3 | Acceptance of wide-angle scattering |
| Evaluation and illustration of the results supported by automation | |

The zero positions from the adjustments can be deposited in the memory unit, such as the control unit 6; they can be used to derive various measurement profiles.

The zero position and/or the starting values and the positions b for the various profiles in the program based on the automatic adjustment are saved, and during actual measurement of a sample when the threshold value is not reached, routines can proceed automatically. This can, for example, increase the measurement beam intensity and allow for an image that is better to evaluate. So it is possible, even in the case of differing samples without knowing the scattering intensities to be expected, to achieve an image that can be evaluated.

It is noted that units for determining the actual position and/or actual orientation of the individual components 0, 1, 2, 4, 5, 7 are not depicted in the drawing. Respective measurement signals can be obtained by measurement devices of various kinds, which survey the components, or can be obtained via the actuating drives 11 per se, whose respective position can be regarded a measurement value relating to the position and/or orientation of the respective component.

As a point of reference for adjustment, the position of the radiation source 0 or the sample 3 can advantageously be used.

The invention claimed is:

1. A method for examining a sample with radiation emitted from a radiation source selected from the group consisting of a neutron radiation source and an X-ray radiation source, directed to the sample carried by a sample holder via at least one beam-forming unit, detected by a detector and evaluated in an evaluating unit, which comprises the steps of:
   prior to an examination of the sample, performing, via a control device and actuating devices, at least one of orienting and positioning components coupled to the actuating devices and selected from the group consisting of the radiation source, the beam-forming unit, the sample holder, the detector, and a primary beam stop disposed upstream of the detector, in terms of at least one of a spatial location in relation to at least other ones of the components, in relation to a predefined fixed point, or in relation to an optical path;

when performing the step of at least one of orienting and positioning the components, outputting actuating signals from the control device to the at least one actuating drive based on saved adjustment values resulting in an automatic performance of a sequence of steps that adjust spatial positions, tilts, and rotations of the components in a reproducible way; and using a radiation intensity measured by the detector or a value derived from the radiation intensity for establishing a control variable conferred from the control unit to the actuating drives assigned to the components.

2. The method according to claim 1, which further comprises performing one of:

adjusting the components independently to a predefined starting position prior to performing a measurement; or if the components are located in a predefined starting position, using values of a starting adjustment that correspond to the starting position or orientation of the components as starting values for an adjustment.

3. The method according to claim 1, which further comprises:

comparing the radiation intensity determined at the detector or the values derived therefrom with saved set values; and adjusting the components via the actuating drives based on a comparison.

4. The method according to claim 1, which further comprises:

approximating an intensity measured in at least one predefined detector range, during adjustment of the individual components; and determining or using at least one of a signal-noise ratio or an absolute intensity in an integral, two-dimensional image on the detector or an intensity of individual intensity maximums in a scattering image or, when using a one-dimensional detector that is moved across a surveyed angle range, local intensity maximums as the values derived from the radiation intensity measured.

5. The method according to claim 1, wherein for adjustment with respect to a position in space, shifting the components at least one of in a direction of the optical path, in a plane vertical to the optical path, in an orientation with respect to the axis of the optical path, rotated around the axis of the optical path or tilted about the axis of the optical path.

6. The method according to claim 1, which further comprises measuring X-rays impinging on the detector for determining control variables at a plurality of different detector ranges.

7. The method according to claim 1, which further comprises:

selecting the at least one beam-forming unit from the group consisting of beam-forming optics and beam-limiting optics; and measuring the radiation intensity measured by the detector in a predefined detector range.

8. The method according to claim 4, which further comprises approximating a maximum value of the intensity measured in the at least one predefined detector range.

9. A device for radiographic examination of samples, comprising:

a radiation source selected from the group consisting of a neutron radiation source and an X-ray radiation source;
at least one beam-forming unit;
a detector;
a sample holder disposed between said radiation source and said detector;
a beam limiting unit;
at least one actuating drive for at least one of orientating or positioning at least one component selected from the group consisting of said radiation source, said beam-forming unit, said beam limiting unit, said sample holder and said detector, said at least one component connected and adjusted by said at least one actuating drive; and a control device outputting actuating signals to said at least one actuating drive based on saved adjustment values resulting in an automatic performance of a sequence of steps that adjust a spatial position, tilt, and rotation of said at least one component in a reproducible way, said control unit having a further input for receiving measured values of radiation intensities determined in at least one predefined detector range of said detector or values derived therefrom and produces the actuating signals based on the values of the radiation intensities measured.

10. The device of according to claim 9, wherein:

said component is one of a plurality of components selected from the group consisting of said radiation source, said beam-forming unit, said beam limiting unit, said sample holder and said detector;

said at least one actuating drive is one of a plurality of actuating drives each connected to and adjusting one of said components; and said control unit has an input for receiving actual adjustment values corresponding to at least one of a respective orientation or position of said components, wherein the actual adjustment values are either present saved on memories, can be determined by measurement units connected to said control unit, or provided by said actuating drives.

11. The device of according claim 9, wherein:

said component is one of a plurality of components selected from the group consisting of said radiation source, said beam-forming unit, said beam limiting unit, said sample holder and said detector;

said at least one actuating drive is one of a plurality of actuating drives each connected to and adjusting one of said components; and said control unit has a comparator, by said comparator measurement values of the radiation intensity determined in predefined detector ranges can be compared with actual adjustment values saved or determined for said components.

12. The device of according to claim 9, wherein said at least one beam-forming unit is selected from the group consisting of beam-forming optics and beam-limiting optics;

further comprising a primary beam stop disposed upstream of said detector; and wherein said component is one of a plurality of components selected from the group consisting of radiation source, said at least one beam-forming unit, said a detector, said sample holder and said primary beam stop;

wherein said at least one actuating drive is one of a plurality of actuating drives, each of said actuating drives connected to and adjusting one of said components.

13. The device according to claim 12, wherein, for adjustment of said beam-forming optics or said beam-limiting optics, said optics are provided in a form of at least one of diaphragms insertable or tiltable into an optical path or adjustable with respect to a gap width.

14. The device according to claim 12, wherein said beam-forming optics or said beam-limiting optics and said radiation source are at least one of shiftable relative to one another in three spatial dimensions, rotatable around an optical axis or an optical path, or supported in a tiltable manner and adjustable in a driven manner by said actuating drives.

15. The device according to claim 12, further comprising at least one of a carrier unit insertable into an optical path in a plane perpendicular to the optical path or a tiltable carrier unit tiltable into the optical path, at least one of said sample holder, the sample or said primary beam stop is carried by said carrier unit or said tiltable carrier unit.

16. The device according to claim 12, wherein a distance between said sample holder and said detector is adjustable using said actuating drives assigned to said components depending on a measured value of the radiation intensity or the value derived therefrom.

* * * * *